US010143817B2

(12) United States Patent
Chodkowski et al.

(10) Patent No.: US 10,143,817 B2
(45) Date of Patent: Dec. 4, 2018

(54) CUSHION HAVING ADJUSTABLE STABILIZATION MEMBER

(71) Applicant: KONINKLIJKE PHILIPS N.V., Eindhoven (NL)

(72) Inventors: Lauren Patricia Chodkowski, Pittsburgh, PA (US); Peter Chi Fai Ho, Pittsburgh, PA (US); Robert William Baiko, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 703 days.

(21) Appl. No.: 14/361,471

(22) PCT Filed: Nov. 27, 2012

(86) PCT No.: PCT/IB2012/056762
§ 371 (c)(1),
(2) Date: May 29, 2014

(87) PCT Pub. No.: WO2013/084110
PCT Pub. Date: Jun. 13, 2013

(65) Prior Publication Data
US 2014/0366886 A1    Dec. 18, 2014

Related U.S. Application Data

(60) Provisional application No. 61/567,146, filed on Dec. 6, 2011.

(51) Int. Cl.
*A61M 16/06* (2006.01)

(52) U.S. Cl.
CPC ........ *A61M 16/0622* (2014.02); *A61M 16/06* (2013.01); *A61M 16/0605* (2014.02);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS

| 601,074 | A | * | 3/1898 | Graham | ................ | A61M 16/06 |
| | | | | | | 128/203.29 |
| 2,336,979 | A | * | 12/1943 | Boothby | .............. | A62B 18/025 |
| | | | | | | 128/201.19 |

(Continued)

FOREIGN PATENT DOCUMENTS

| FR | 2397199 A1 | * | 2/1979 | ............ | A61M 16/06 |
| WO | WO 9921602 A1 | * | 5/1999 | .......... | A61M 15/009 |

(Continued)

*Primary Examiner* — Rachel T Sippel
*Assistant Examiner* — Tu Vo
(74) *Attorney, Agent, or Firm* — Michael W. Haas

(57) ABSTRACT

A cushion assembly (16) for use in a patient interface device (10) includes a cushion member having a sealing flap (24) adapted to sealing engage a user's face about at least one of an oral orifice or nasal orifices of the user. The cushion member defines a cavity (30) therein accessible via an opening generally defined by the sealing flap. The cushion assembly further includes a stabilizing member (16b) having a first end and an opposite second end, the first end and the second end being selectively coupled to the sealing flap such that the stabilizing member spans across at least a portion of the opening.

2 Claims, 6 Drawing Sheets

(52) U.S. Cl.
CPC ..... *A61M 16/0616* (2014.02); *A61M 16/0633* (2014.02); *A61M 2016/0661* (2013.01); *A61M 2210/0606* (2013.01); *A61M 2210/0618* (2013.01)

(58) Field of Classification Search
CPC .......... A61M 16/0627; A61M 16/0633; A61M 16/0638; A61M 16/0644; A61M 16/065; A61M 16/0655; A61M 2016/0661; A61M 16/0683; A61M 2210/0606; A61M 2210/0618; A62B 18/00; A62B 18/02; A62B 18/025; A62B 18/04; A62B 18/045; A62B 18/06; A62B 18/08
See application file for complete search history.

(56) References Cited

U.S. PATENT DOCUMENTS

| | | | | |
|---|---|---|---|---|
| 2,403,046 | A * | 7/1946 | Bulbulian | A62B 18/025 128/201.19 |
| 2,415,846 | A | 2/1947 | Randall | |
| 2,578,621 | A | 12/1951 | Yant | |
| 2,868,195 | A * | 1/1959 | Finken | A62B 18/025 128/204.17 |
| 2,875,757 | A * | 3/1959 | Galleher, Jr. | A61M 16/0683 128/206.26 |
| 2,998,818 | A * | 9/1961 | Tabor | A61M 16/06 128/207.11 |
| 5,143,061 | A * | 9/1992 | Kaimer | A41D 13/1146 128/205.25 |
| D334,633 | S * | 4/1993 | Rudolph | D24/110.4 |
| 5,265,595 | A * | 11/1993 | Rudolph | A61B 5/097 128/204.18 |
| 5,540,223 | A * | 7/1996 | Starr | A61M 16/06 128/205.25 |
| 6,082,360 | A * | 7/2000 | Rudolph | A61M 16/06 128/206.24 |
| 2002/0122746 | A1* | 9/2002 | Yamamori | G01N 1/22 422/83 |
| 2003/0024533 | A1* | 2/2003 | Sniadach | A61M 16/06 128/205.25 |
| 2011/0247628 | A1* | 10/2011 | Ho | A61M 16/06 128/206.28 |
| 2013/0131533 | A1* | 5/2013 | Orr | A61M 16/06 600/532 |

FOREIGN PATENT DOCUMENTS

| | | | |
|---|---|---|---|
| WO | WO9921602 A1 | 5/1999 | |
| WO | WO 2011030250 A1 * | 3/2011 | ............ A61M 16/06 |
| WO | WO 2011080641 A2 * | 7/2011 | ............ A61M 16/06 |
| WO | WO2011080641 A2 | 7/2011 | |

\* cited by examiner

CUSHION HAVING ADJUSTABLE STABILIZATION MEMBER

CROSS-REFERENCE TO RELATED APPLICATIONS

This patent application claims the priority benefit under 35 U.S.C. § 371 of international patent application no. PCT/IB2012/056762 filed Nov. 27, 2012, which claims the priority benefit under 35 U.S.C. § 119(e) of U.S. Provisional Application No. 61/567,146 filed on Dec. 6, 2011, the contents of which are herein incorporated by reference.

BACKGROUND OF THE INVENTION

1. Field of the Invention

The present invention generally relates to cushion assemblies for use on a patient interface device in a pressure support system that supplies a flow of gas to the airway of a patient, and, more particularly, to cushion assemblies which include one or more adjustable stabilization members. The invention further relates to patient interface devices that include such cushion assemblies.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask (i.e., a full face mask), on the face of a patient to interface the ventilator or pressure support system with the airway of the patient so that a flow of breathing gas can be delivered from the pressure/flow generating device to the airway of the patient.

Typically, patient interface devices include a mask shell having a cushion attached to the shell that contacts, and seals against, the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provide a tight enough seal against a patient's face without discomfort.

Full face CPAP masks that include one chamber that covers the nose and mouth have a single opening in the sealing flap to accommodate both the nose and mouth. In encompassing both the nose and mouth, the sealing perimeter of a full face mask must cover a large area wherein the anatomical contours typically vary significantly. Such varying contours can make the seal more susceptible to stability and leak issues. Accordingly, considerable forces are often necessary in order to achieve a satisfactory seal. Such forces generally make such masks uncomfortable to wear, particularly for extended periods of time.

SUMMARY OF THE INVENTION

It is therefore an object of the present invention to provide cushion assemblies and patient interface devices that overcome shortcomings of existing devices.

In one example embodiment of the present invention a cushion assembly for use in a patient interface device is provided. The cushion assembly comprises a cushion member having a sealing flap adapted to sealing engage a user's face about at least one of an oral orifice or nasal orifices of the user. The cushion member defines a cavity therein accessible via an opening generally defined by the sealing flap. The cushion assembly further comprises a stabilizing member having a first end and an opposite second end. The first end and the second end are selectively coupled to the sealing flap such that the stabilizing member spans across at least a portion of the opening.

The stabilizing member may be adapted to be disposed between the nose and mouth of a user when the sealing flap is sealingly engaged with the user's face.

The stabilizing member may be adapted to be disposed on or about the bridge of a user's nose when the sealing flap is sealingly engaged with the user's face.

The first end of the stabilization member may be moveable among a plurality of positions on a first side of the opening and the opposite second end of the stabilization member may be moveable among a plurality of positions on an opposite second side of the opening.

The sealing flap may include a first plurality of protruding members extending therefrom on a first side of the opening and a second plurality of protruding members extending therefrom on a second side of the opening. The first end of the stabilization member may be adapted to be selectively coupled to at least one of the first plurality of protrusions and the opposite second end of the stabilization member may be adapted to be selectively coupled to at least one of the second plurality of protrusions.

In another example embodiment of the present invention a patient interface device is provided. The patient interface device comprises a mask shell and a cushion assembly. The cushion assembly comprises a cushion member including a first end portion having a sealing flap adapted to sealingly engage a user's face about at least one of an oral orifice or nasal orifices of a user and a second end portion generally opposite the first end portion coupled to the mask shell. The cushion member defining a cavity therein accessible via an opening generally defined by the sealing flap. The cushion assembly further comprises a stabilizing member having a first end and an opposite second end, the first end and the second end being selectively coupled to the sealing flap such that the stabilizing member spans across at least a portion of the opening.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
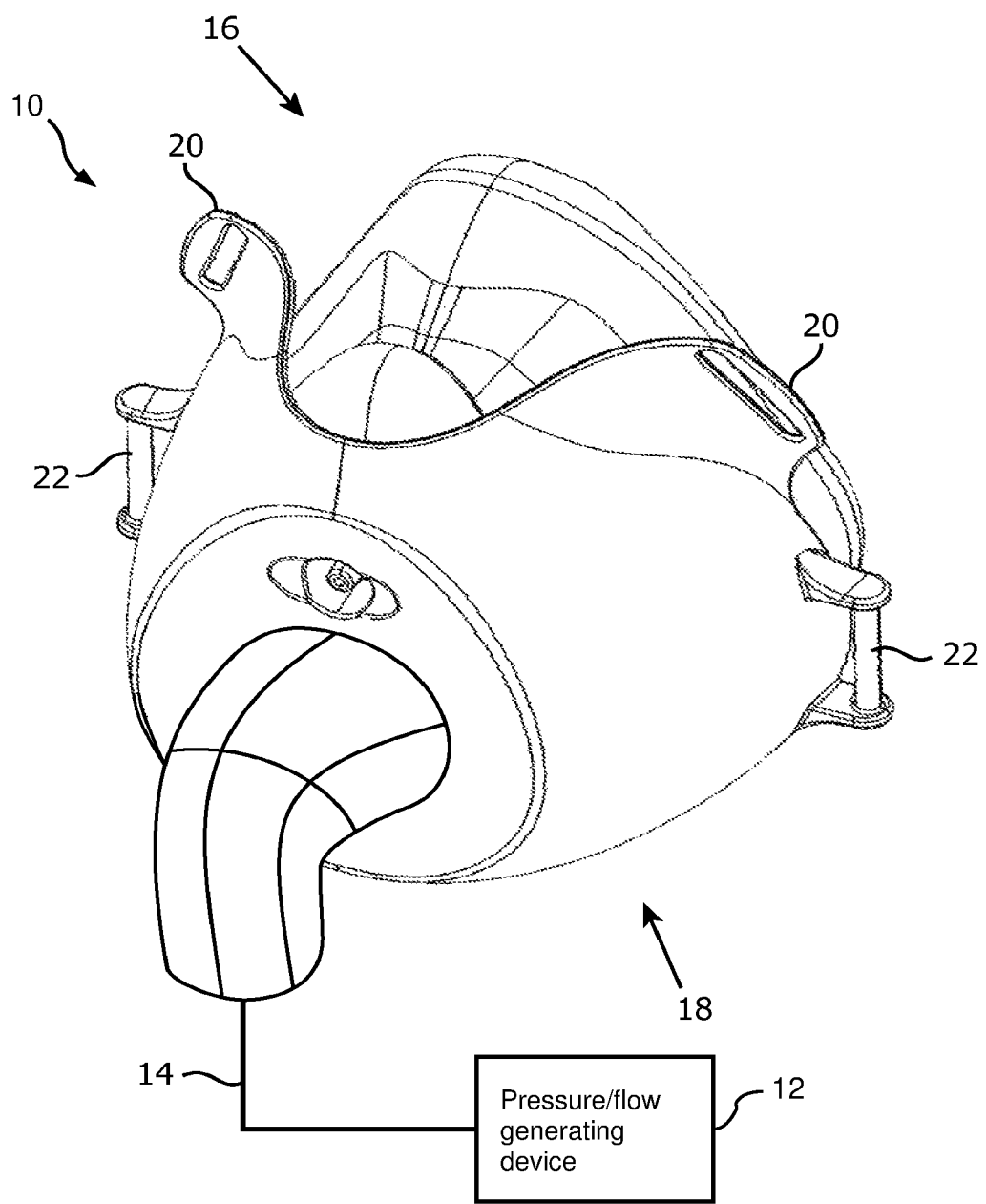
FIG. 1 is a front isometric view of an embodiment of a patient interface device according to the principles of the present invention shown (schematically) connected to a gas flow/pressure generating system to form a patient interface system.
Figure 2:
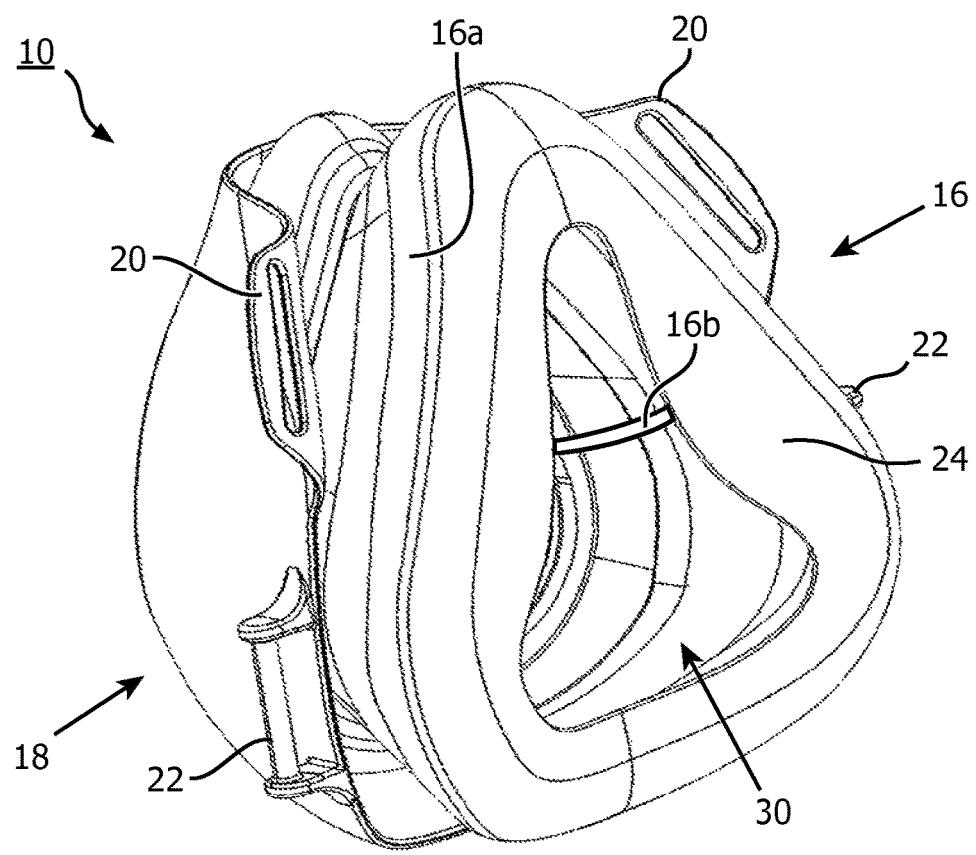
FIG. 2 is a rear isometric view of the patient interface device of FIG. 1.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the phrase that two or more elements are "selectively coupled" shall mean the elements are coupled in a manner that may be readily positioned in either of a coupled or uncoupled position.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIGS. 1-6 illustrate an exemplary embodiment of a patient interface device 10 and components thereof according to the principles of the present invention. Patient interface device 10 communicates a flow of breathing gas between the patient's airway and a pressure/flow generating system 12 (shown schematically), such as a ventilator, CPAP device, or variable pressure device, e.g., a BiPAP® device manufactured and distributed by Philips Respironics, Inc. of Pittsburgh, Pa., or an auto-titration pressure support system.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating system 12 is also referred to as a gas flow generating device, because flow results when a pressure gradient is generated. The present invention contemplates that pressure/flow generating system 12 is any conventional system for delivering a flow of gas to an airway of a patient or for elevating a pressure of gas at an airway of the patient, including the pressure support systems summarized above and non-invasive ventilation systems.

Communicating a flow of breathing gas between the patient's airway and pressure/flow generating system 12 includes delivering a flow of breathing gas to the patient from the pressure/flow generating device and exhausting a flow of gas from the patient to ambient atmosphere. The system for delivering a breathing gas to a patient according to the present invention comprises the pressure/flow generating system that produces a flow of gas, and a conduit 14, which is also referred to as a patient circuit, having a first end portion (not numbered) operatively coupled to the gas flow generating device and a second end portion (not numbered). Conduit 14 carries the flow of gas from pressure/flow generating device 12 during operation of the system to patient interface device 10, which is coupled to the second end portion of the conduit. Conduit 14 corresponds to any conduit suitable for communicating the flow of gas form the pressure/flow generating system to the patient interface device. A typical conduit is a flexible tube. A headgear assembly, which is not shown in the figures, attaches patient interface device 10 to the patient's head.

Patient interface device 10 includes a cushion assembly, generally indicated at 16, and a mask shell 18 having a patient side and opposite thereto, an outer side. Attached to outer side of mask shell 18 is a conduit coupling member (not numbered) that couples mask shell 18 to conduit 14 so that a flow of gas is communicated to the interior of the patient interface device for subsequent delivery to the patient. Conversely, gas from the patient is communicated from the patient interface device into conduit 14, where an exhaust port is located. Mask shell 18 is preferably a generally rigid shell, and, in an exemplary embodiment of the present invention is formed from rigid plastic, such as polycarbonate. It is to be understood that the present invention contemplates that one or more of the size, shape, or composition of mask shell 18 may be varied without varying from the scope of the present invention.

In the illustrated embodiment of FIG. 1, mask shell 18 has a generally rounded triangular shape and is provided with upper and lower headgear attaching elements 20, 22, which cooperate with corresponding attachment elements on headgear straps (not illustrated). It is to be understood that the present invention contemplates using any conventional connection assembly to attach a headgear or headgear strap to mask shell 18 or other suitable shell arrangement. It is to be further understood that the present invention also contemplates that mask shell 18 may further include a forehead support portion having headgear attaching elements for connection to further headgear straps. The present invention also contemplates providing a post or other protrusion at the upper portion of the shell, i.e., the portion overlying the bridge of the nose, to which the headgear can be attached.

The present invention contemplates that the headgear suitable for use with patient interface device 10 is any conventional headgear used in the patient interface field. For example, without limitation, a typical headgear assembly comprises a headpiece that overlies a portion of the patient's crania and with headgear straps extending therefrom to adjustably connect the headgear to the mask.

Figure 3:
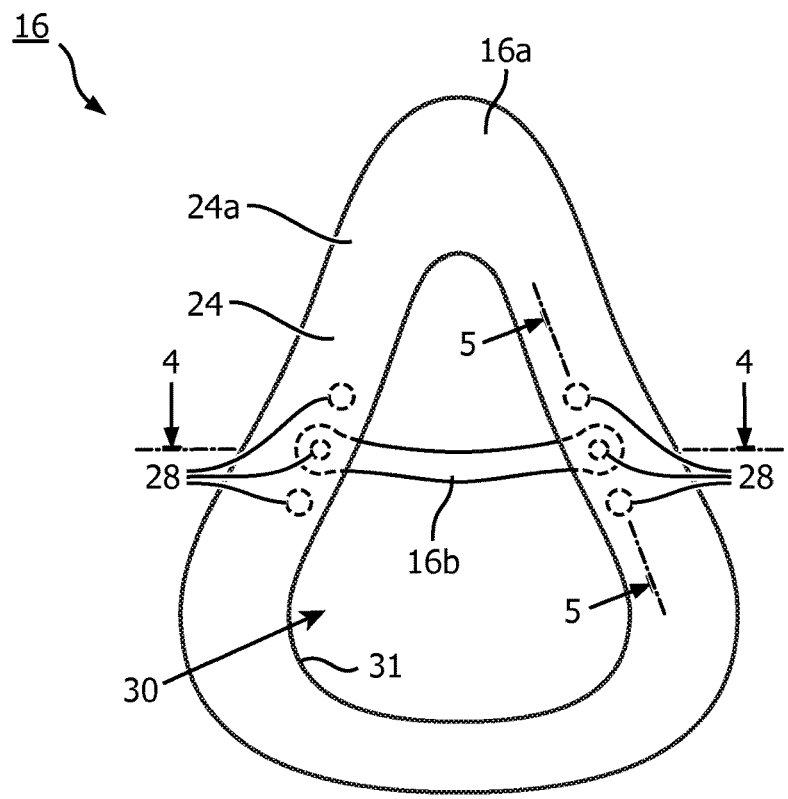
FIG. 3 is a rear (patient side) elevational view of the cushion assembly of the patient interface device of FIGS. 1 and 2.
Figure 4:
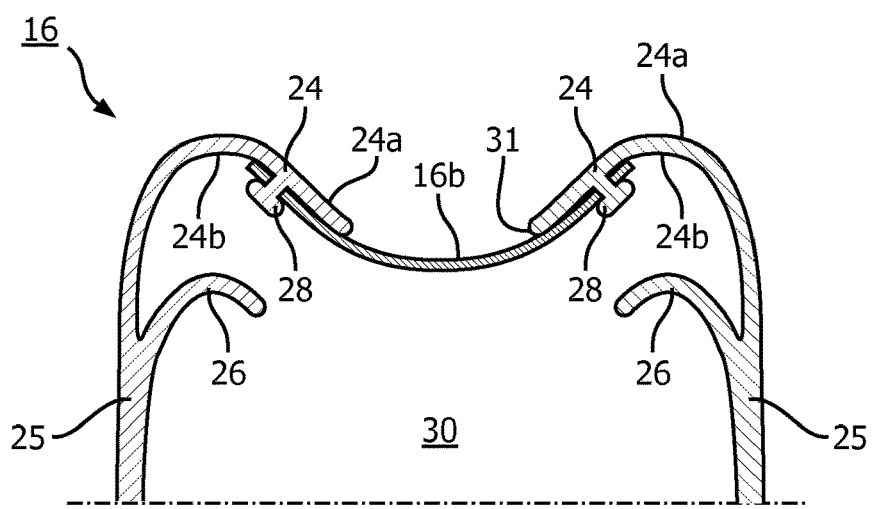
FIG. 4 is a sectional view of the cushion assembly of the patient interface device of FIGS. 1 and 2 taken along line 4-4 of FIG. 3.
Figure 5:
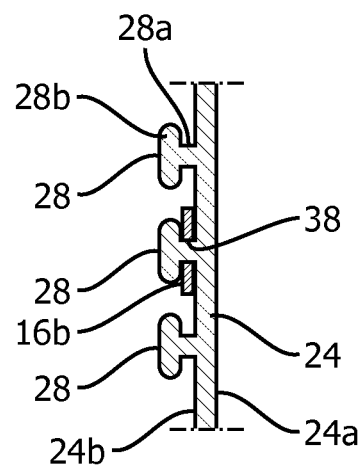
FIG. 5 is a sectional view of a portion of the cushion assembly of the patient device of FIGS. 1 and 2 taken along line 5-5 of FIG. 3.

Referring to FIGS. 3-5, cushion assembly 16 includes a cushion member 16a and a stabilizing member 16b. Cushion member 16a is preferably formed of a soft, cushiony, elastomeric material, such as silicone, appropriately soft thermoplastic elastomers, closed cell foam, thin materials, or any combination of suitable materials. Cushion member 16a includes a first end portion having a sealing flap 24 adapted to sealingly engage a user's face about the mouth and nose of the user when patient interface device 10 is donned on the head of a user and a second end portion (not numbered) generally opposite the first end portion that is adapted to be coupled to a mask (such as mask shell 18 in FIGS. 1 and 2). Cushion member 16a further includes a wall portion 25 which extends between the first and second end portions and generally defines a cavity 30 (FIGS. 2-4) therein accessible via an opening 31 (FIGS. 3 and 4) disposed adjacent, and generally defined by sealing flap 24.

As shown in the cross-sectional view of FIG. 4, cushion member 16a may also include a inner support portion 26, however, it is to be understood that cushion assembly may be formed with or without other structures aside from sealing flap 24, such as, for example, without limitation, inner support portion 26, without varying from the scope of the present invention.

Referring to the cross-sectional views of FIGS. 4 and 5, sealing flap 24 includes an outer surface 24a adapted to be in contact with the face of a user and an opposite inner surface 24b adapted to generally face away from the face of a user. Continuing to refer to the cross-sectional views of FIGS. 4 and 5, inner surface 24b includes a number (two sets of three in the illustrated embodiment) of coupling members 28 extending therefrom. In the illustrated embodiment, each coupling member 28 is formed as a generally T-shaped member having a stem portion 28a which extends from inner surface 24b of sealing flap 24 and a top portion 28b oriented generally perpendicular to stem portion 24b.

Figure 6:
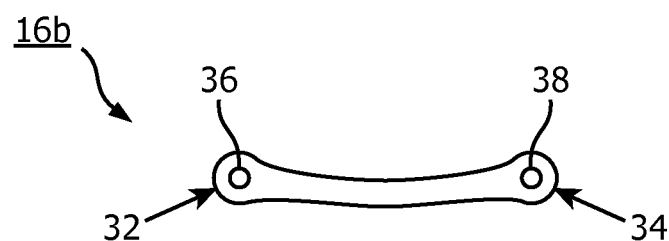
FIG. 6 is an elevational view of the stabilizing member of the cushion assembly of the patient interface device of FIGS. 1 and 2.

Referring to FIG. 6, stabilizing member 16b is formed separately from cushion member 16a and is preferably formed from a somewhat elastic, flexible material (e.g., without limitation, silicone or other suitable material) and includes a first end 32 and an opposite second end 34. Each of first and second ends 32 and 34 are selectively coupled to sealing flap 24 such that stabilizing member 16b spans across at least a portion of opening 31. As shown in the example arrangement of FIG. 3, each of first and second ends 32 and 34 include apertures 36 and 38 which are each cooperatively sized to be selectively coupled to a respective coupling member 28 disposed on either side of opening 31. It is to be appreciated that by spanning across at least a portion of opening 31, stabilizing member acts to stabilize the sides (not numbered) of sealing flap 24 (and thus cushion member 16a) in a manner that helps to keep the sides from deforming in a manner that would compromise the seal between sealing flap 24 and the face of a user. It is also to be appreciated that in addition helping to stabilize cushion member 16a, stabilizing member 16b also may provide guidance for positioning of cushion assembly 16 on the face of a user.

As shown in the example embodiment of FIG. 3, stabilizing member 16b may be positioned such that when sealing flap 24 is sealingly engaged with the user's face stabilizing member 16b is disposed generally between the nose and mouth of a user. As an alternative or further enhancement, stabilizing member 16b may be positioned to be generally disposed on or about the bridge of a user's nose when sealing flap 24 is sealingly engaged with the user's face.

In order to provide for optimum comfort and sealing ability of sealing flap 24 and the face of a user, stabilization member 24 is preferably adjustably coupled to inner surface 24b of sealing flap 24. In the illustrated example embodiment, such adjustability is provided via the plurality of coupling members 28 to which each of first and second ends 32 and 34 of stabilizing member 16b may be coupled depending on the location with respect to opening 31, and thus points of concern on a user's face, it is desired to place stabilizing member 16b for optimum comfort and/or sealing of cushion assembly 16 with respect to the user.

Although shown in the illustrated embodiment as being coupled through the interaction of T-shaped members and cooperatively sized apertures, it is to be understood that such coupling mechanisms are provided for example purposes only and are not intended to be limiting upon the scope of the present invention as the present invention contemplates that other coupling mechanisms in addition to those particularly described herein may be suitably employed to selectively couple stabilizing member 16b to sealing flap 24.

Figure 7A:
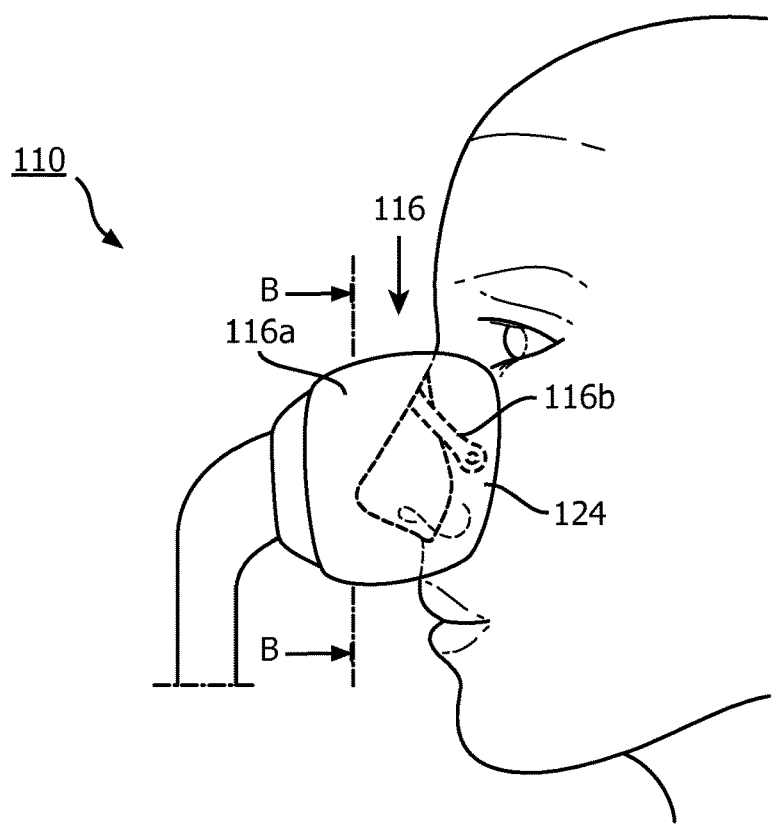
FIG. 7A is a side elevational view of another embodiment of a patient interface device according to the principles of the present invention disposed on the head of a user.
Figure 7B:
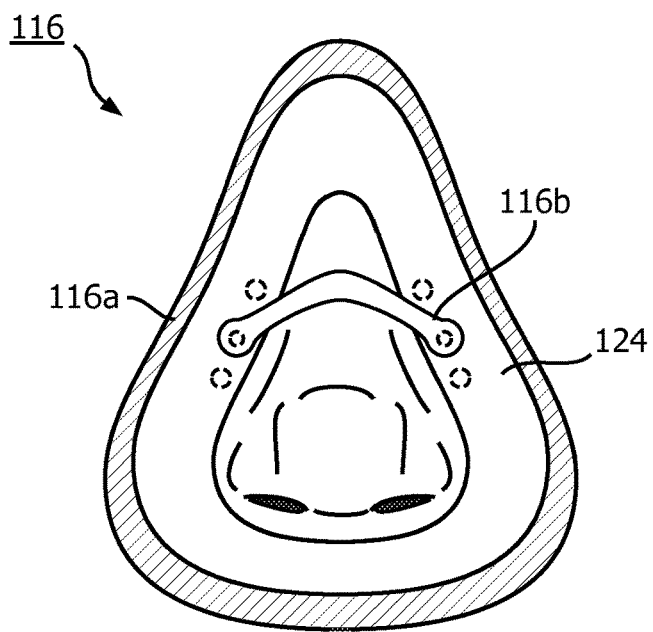
FIG. 7B is a sectional view of the cushion assembly of the patient interface device of FIG. 7A taken along line B-B of FIG. 7A.

FIGS. 7A and 7B illustrate another example embodiment of a patient interface device 110 according to the principles of the present invention disposed on the head of a user. Unlike cushion assembly 16 (previously described) which encompassed both a user's mouth and nose, patient interface device 110 utilizes a cushion assembly 116 that encompasses only a user's nose (not numbered). Like cushion assembly 16, cushion assembly 116 includes a cushion member 116a and a stabilizing member 116b adjustably selectively coupled to, and spanning across an opening (not numbered) formed in, a sealing flap 124 formed at a patient end (not numbered) of cushion member 116a which helps to stabilize sealing flap 124, and thus cushion member 116a, on the user's face on and about the user's nose.

Figure 8A:
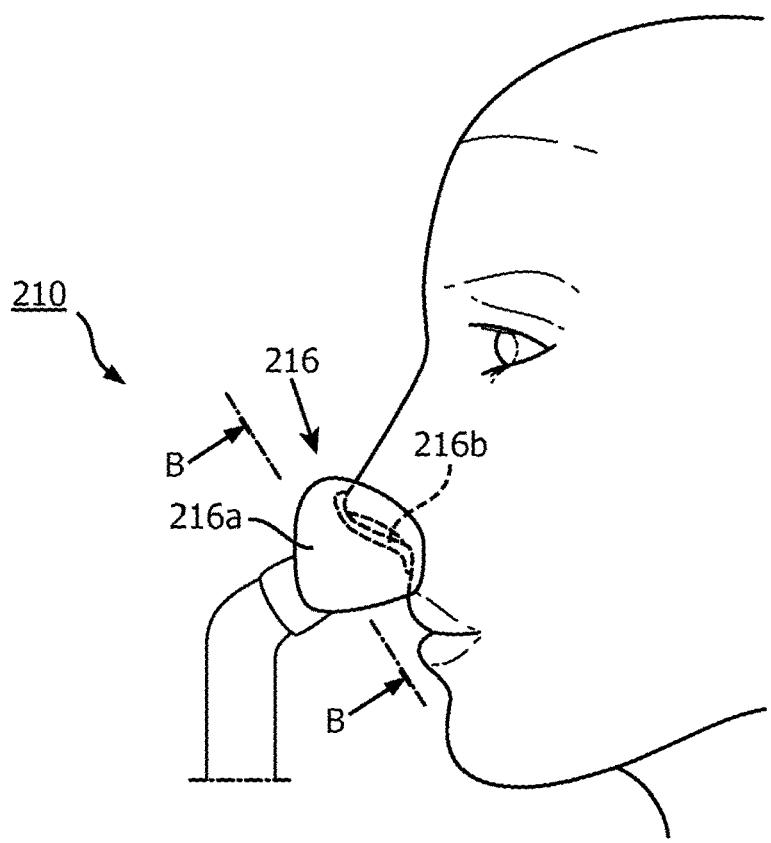
FIG. 8A is a side elevational view of yet another embodiment of a patient interface device according to the principles of the present invention disposed on the head of a user.
Figure 8B:
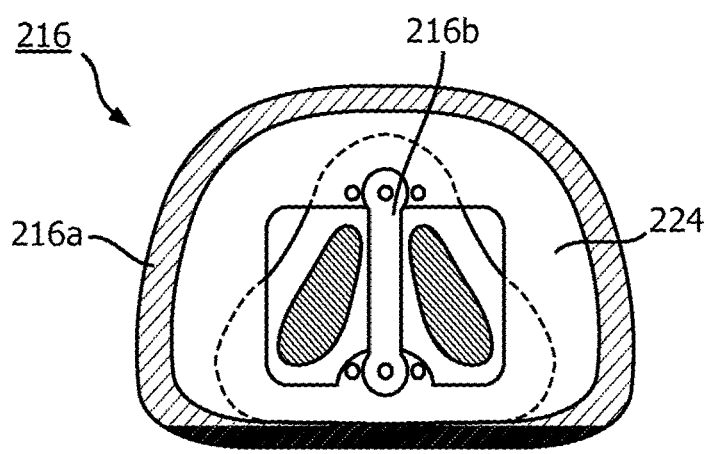
FIG. 8B is a sectional view of the cushion assembly of the patient interface device of FIG. 8A taken along line B-B of FIG. 8A.

FIGS. 8A and 8B illustrate yet another example embodiment of a patient interface device 210 according to the principles of the present invention disposed on the head of a user. Like patient interface device 110, patient interface device 210 utilizes a cushion assembly 216 that encompasses only a user's nose (not numbered) and includes a cushion member 216a and a stabilizing member 216b adjustably selectively coupled to a sealing flap 224 formed at a patient end (not numbered) of cushion member 216a. Unlike cushion assembly 116 in which stabilizing member 116 was disposed generally across the opening in sealing flap 124 in a generally horizontal position, stabilizing member 216b of cushion member 216 spans the opening in sealing flap 224 in a generally vertical manner. It is to be appreciated that such arrangement helps to stabilize the top and bottom portions of cushion member 216a while also providing a positioning mechanism for helping to align cushion assembly 216 on the nose of a user (stabilizing member 216b is aligned between the nostrils of the user).

Although the example embodiments illustrated herein depict the use of only a single stabilizing member, it is to be understood that the present invention also contemplates the use of multiple adjustable stabilizing members depending on the particular application. For example, without limitation, a second stabilizing member disposed to span across the bridge of a user's nose could be added to the example embodiment illustrated in FIGS. 1-6 to add further stability to an upper portion of full face cushion assembly 16.

It is to be appreciated that the present invention is not intended to be limited to the mask or cushion shapes described herein but instead may be employed with masks and cushion of various other shapes or designs as long as the dampening portion is disposed generally between a stiffened portion of the cushion wall and the mask. It can be further appreciated that the present invention provides a patient interface device that improves upon existing devices, for example, to maximize patient comfort while minimizing leak, during delivery of a positive airway pressure or flow of gas to the airway of the user.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion assembly for use in a patient interface device, the cushion assembly comprising:
    a cushion member having a sealing flap adapted to sealingly engage a user's face about at least one of an oral orifice or nasal orifices of the user, the cushion member defining a cavity therein accessible via an opening defined by the sealing flap; and
    a stabilizing member having a first end and an opposite second end;
    wherein the sealing flap comprises:
        an outer surface which is adapted to sealingly engage the user's face about at least one of the oral orifice or nasal orifices of the user;
        an inner surface disposed opposite the outer surface;
        a first plurality of protruding members extending from the inner surface on a first side of the opening;
        a second plurality of protruding members extending from the inner surface on a second side of the opening;
    wherein the first end of the stabilizing member is selectively coupled to at least one of the first plurality of protruding members and the opposite second end of the stabilization member is selectively coupled to at least one of the second plurality of protruding members such that the stabilizing member spans across at least a portion of the opening and is sized and configured to be disposed between the cavity and the user's face when the sealing flap is sealingly engaged with the user's face;
    wherein the stabilizing member is structured to stabilize the sealing flap about first side and the second side of the opening; and
    wherein the stabilizing member is adapted to be disposed on a bridge of the user's nose when the sealing flap is sealingly engaged with the user's face.

2. The cushion assembly of claim 1, wherein the first end of the stabilization member is moveable among a plurality of positions on a first side of the opening and wherein the opposite second end of the stabilization member is moveable among a plurality of positions on an opposite second side of the opening.

* * * * *